(12) United States Patent
Herndon (10) Patent No.: US 8,150,505 B2
(45) Date of Patent: Apr. 3, 2012

(54) METHOD AND APPARATUS FOR THE FORMATION OF MULTIPLE MICROCONDUITS

(75) Inventor: Terry O. Herndon, Carlisle, MA (US)

(73) Assignees: Path Scientific, LLC, Carlisle, MA (US); Galderma Pharma S.A., Cham (CH)

( * ) Notice: Subject to any disclaimer, the term of this patent is extended or adjusted under 35 U.S.C. 154(b) by 1137 days.

(21) Appl. No.: 11/743,818

(22) Filed: May 3, 2007

(65) Prior Publication Data

US 2008/0275378 A1 Nov. 6, 2008

(51) Int. Cl.
- *A61B 5/05* (2006.01)
- *A61B 17/50* (2006.01)
- *A61B 17/20* (2006.01)
- *A61M 37/00* (2006.01)

(52) U.S. Cl. ............................ 600/547; 604/46; 606/131

(58) Field of Classification Search .................. 600/547, 600/562, 564, 569, 570; 604/46; 606/131
See application file for complete search history.

(56) References Cited

U.S. PATENT DOCUMENTS

| | | | |
|---|---|---|---|
| 3,756,242 A * | 9/1973 | Coss | 606/167 |
| 4,523,580 A | 6/1985 | Tureaud | |
| 6,235,039 B1 | 5/2001 | Parkin et al. | |
| 6,264,666 B1 | 7/2001 | Coleman et al. | |
| 6,277,128 B1 | 8/2001 | Muldner | |
| 6,299,620 B1 | 10/2001 | Shadduck et al. | |
| 6,306,147 B1 | 10/2001 | Bernabei et al. | |
| 6,387,103 B2 | 5/2002 | Shadduck | |
| 6,432,113 B1 | 8/2002 | Parkin et al. | |
| 6,503,256 B2 | 1/2003 | Parkin et al. | |
| 6,629,983 B1 | 10/2003 | Ignon | |
| 6,706,032 B2 | 3/2004 | Weaver et al. | |
| 6,726,693 B2 | 4/2004 | Weber et al. | |
| 6,764,493 B1 | 7/2004 | Weber et al. | |
| 6,926,681 B1 | 8/2005 | Ramey et al. | |
| 6,942,649 B2 | 9/2005 | Ignon et al. | |
| 2004/0204700 A1 | 10/2004 | Weaver et al. | |
| 2006/0041241 A1* | 2/2006 | Herndon | 604/500 |
| 2007/0088248 A1 | 4/2007 | Glenn et al. | |

FOREIGN PATENT DOCUMENTS

WO 2007/028167 A2 3/2007

OTHER PUBLICATIONS

Ciocon, David et al., How Low Should You Go: Novel Device for Nail Trephination, American Society for Dermatologic Surgery, Inc., Jun. 2006, pp. 828-833, 32:6, Blackwell Publishing.
Herndon, Terry O., et al., Transdermal Microconduits by Microscission for Drug Delivery and Sample Acquisition, BMC Medicine, Apr. 19, 2004, http://www.biomedcentral.com/1741-7015/2/12, 2:12, BioMed Central Ltd.
Office Action—China Appln. No. 200880014614.8, Feb. 24, 2011.
Office Action—Canada Appln. No. 2684861 dated Oct. 19, 2011.

* cited by examiner

*Primary Examiner* — Max Hindenburg
*Assistant Examiner* — Jonathan M Foreman (57) ABSTRACT

Disclosed is an apparatus that creates a number of microconduits, i.e., small holes in the stratum corneum, the outermost layer of human skin tissue, to provide a pathway therethrough, which can be used, for example, for transdermal drug delivery.

17 Claims, 4 Drawing Sheets

FIG. 1

PRIOR ART

METHOD AND APPARATUS FOR THE FORMATION OF MULTIPLE MICROCONDUITS

FIELD OF THE INVENTION

Disclosed is an apparatus that creates a number of microconduits, i.e., small holes in the stratum corneum, the outermost layer of skin tissue, to provide a pathway therethrough, which can be used, for example, for transdermal drug delivery.

BACKGROUND OF THE INVENTION

Transdermal drug delivery, as the term is used generally, refers to permeation of the stratum corneum, the tough outer barrier of the skin, by a pharmaceutically active molecule. The stratum corneum, the thin (approximately 20 μm) outer layer of the epidermis, is dead tissue containing both multi-lamellar lipid barriers, and tough protein-based structures.

The epidermis, directly beneath the stratum corneum, also behaves as a lipid barrier. The dermis, directly beneath the epidermis, is permeable to many types of solutes. In the administration of a drug by topical application to skin, lipid-soluble drug molecules dissolve into and diffuse through the skin's multilamellar lipid bilayer membranes along a concentration gradient by virtue of the drug molecules' solubility in the lipid bilayer. Transdermal drug delivery may be targeted to a tissue directly beneath the skin, or to capillaries for systemic distribution within the body by the circulation of blood.

The term "transdermal drug delivery" usually excludes hypodermic injection, long term needle placement for infusion pumps, and other needles which penetrate the skin's stratum corneum. Thus, transdermal drug delivery is generally regarded as minimally invasive. However, the low rate of transport of therapeutic molecules through the stratum corneum remains a common clinical problem.

Transdermal delivery of only a limited number of lipophilic drugs is commercially available. Existing methods include, for example, the use of wearable "patches," a passive transdermal drug delivery method that tends to be slow, and difficult to control.

Another method includes the use of a "gene gun," to accelerate 20 to 70 μm diameter drug particles, or smaller DNA-coated gold particles, to supersonic velocities, such that the particles pass through the stratum corneum into the epidermis or dermis. A single particle, 20 μm to 70 μm, in diameter, such as used in the gene gun, when fired at the stratum corneum at supersonic speeds, ruptures and tears through the tissues of the stratum corneum, epidermis and dermis, stopping and remaining at some depth which is determined by the initial velocity and mass of the particle. The resulting path through the above-mentioned tissues may be in the range of 1 μm to perhaps 30 μm because the tissues are elastic to various degrees, depending on the individual. The semi-static analogue is to pierce a rubber sheet with a common pin, 750 μm in diameter. When pulled out of the rubber sheet, the resultant opening size is less than 1 μm, or perhaps not open at all. This is because the pin has torn the rubber sheet and pushed it aside, due to the rubber sheet's elasticity (ability to get out of the way), as the pin is forced through. As in the analogue, because of the elasticity of skin, use of the gene gun does not form microconduits in the skin because the tissue is only temporarily pushed aside as a particle is forced through the skin.

Examples of transdermal drug delivery methods presently being investigated include the use of ultrasound (sonophoresis) to cause cavitation in the stratum corneum; laser ablation of a small region of the stratum corneum, thereby providing access to the epidermis; the use of microneedles to create openings in the stratum corneum; the use of electrical methods, including low voltage iontophoresis, wherein transport is believed to occur through pre-existing aqueous pathways; and the use of high voltage pulses to cause electroporation of the skin. There are disadvantages associated with each of these methods. For example, often the rate of transport of molecules tends to diminish rapidly with increasing molecular size. Other disadvantages include pain and discomfort, skin irritation, the high cost and the large size of equipment required, and the potential for breaking off needles, which might remain imbedded in the skin.

Also, a common problem encountered in using established techniques such as subcutaneous and intradermal injection to deliver vaccines, is the inaccurate placement of the immunizing material with respect to the epidermal and dermal antigen-presenting cells, or with respect to keratinocytes.

An existing problem with currently used methods of making biopotential measurements and other electrical measurements at the surface of the skin of a living organism is that the measurements are often degraded by motion and by other potentials that are associated with the skin. Techniques such as microscission or stripping of the stratum corneum of the skin can significantly improve the quality of such electrical measurements. However, mechanical alteration of the skin is highly undesirable, because it is difficult to control the degree of alteration; mechanical alteration can cause pain and discomfort, and can lead to infection. Therefore, there is a need for improved methods of making biopotential measurements at the surface of the skin.

The present invention satisfies these needs by providing, for example, an improved method of delivery of therapeutic agents to a tissue; an improved method of transdermal delivery of therapeutic agents; an improved method for delivering therapeutic agents to tissue underlying skin tissue; an improved method for obtaining samples of interstitial fluid or blood for sensing of analytes within the extracted fluid, including the measurement of analytes while within the microconduit; and an improved method of making biopotential measurements.

SUMMARY OF THE INVENTION

Disclosed is an apparatus that creates a number of microconduits, i.e., small holes in the stratum corneum and/or epidermis, the outermost layer of human skin tissue, to provide a pathway therethrough, which can be used, for example, for transdermal drug delivery.

Thus, one embodiment of the present invention is directed to an apparatus for the formation of a single or multiple microconduits by abrasion comprising:

(a) an abrasion assembly, a control module mechanically connected to the abrasion assembly for controlling the depth of the abrasion by a control module for stopping and pulling back the abrading device.

In one embodiment, the abrasion assembly also includes an impedance sensing abrasion unit and a sensor electrically connected to the abrasion assembly.

Preferably, the multiple microconduit forming apparatus includes a mask with a plurality of holes therein and an abrasive disk for the formation of multiple microconduits. The mask can be permanent (e.g., metal) or it can be replaceable (e.g., plastic). In some embodiments, the abrasive disk includes a permanent abrasive material. In other embodiments, the abrasive disk includes a replaceable abrasive material. Still other embodiments include a fine mesh of plastic threads coated with abrasive particles. In other embodiments, the abrasive is made of electrically conducting material.

Preferably, the multiple microconduit forming apparatus includes a mount that allows the impedance sensing abrasion unit to move in a direction perpendicular to the surface being abraded. In another embodiment, the impedance sensing is done by the metal mask contacting interstitial fluid, blood or epidermal tissue. In especially preferred embodiments, the impedance sensing abrasion unit is computer controlled.

Another embodiment of the present invention is directed to a method of forming a plurality of microconduits in a material, which comprises the steps of abrading the material through a mask having a plurality of openings therein, monitoring an electrical impedance of the material being abraded, and stopping the abrading of the material when a change in the electrical impedance of the material is detected. In another embodiment, the diameter of the mask holes and/or thickness of the mask acts to limit the depth of abrasion. In some preferred embodiments, the material being abraded is the stratum corneum and/or superficial epidermal layer of human skin. In other preferred embodiments, the material being abraded is the outer layer of animal skin. Once a plurality of microconduits have been formed, other materials, e.g., drugs, may be readily transported through the microconduits, e.g., as an improvement in transdermal drug delivery.

Yet another embodiment of the present invention is a method of transdermally delivering one or more drugs through the skin of a patient comprising the steps of:

(1) forming a plurality of microconduits through the outer layer of the patient's skin using an abrasion apparatus comprising an abrasion assembly with an abrading device, and a control module mechanically connected to the abrasion assembly for controlling the depth of the abrasion by stopping and pulling back the abrading device; and (2) applying said one or more drugs to the microconduits for transdermal delivery.

BRIEF DESCRIPTION OF THE DRAWINGS

FIG. 2 shows the modifications made to the PATH FORMER device. The drill portion is removed and replaced by a mandrel for an abrasive disk. The disk, when used in conjunction with a multi-hole skin mask, permits the formation of multiple microconduits through the stratum corneum.

DETAILED DESCRIPTION OF THE PREFERRED EMBODIMENT

As set forth above, the present invention is directed to an apparatus that creates a number of microconduits, i.e., small holes in the stratum corneum, the outermost layer of skin tissue, to provide a pathway therethrough, which can be used, for example, for transdermal drug delivery.

In preferred embodiments, the present invention is directed to modified versions of the PATH FORMER™ microconduit drill, which is described in U.S. Patent Publication No. 2006-0041241 A1, the disclosure of which is hereby incorporated herein by reference.

Although the PATH FORMER nicely cuts away the stratum corneum to produce microconduits, transdermal patch drug delivery ideally will require a number of holes in a small area for maximum drug flux across the skin.

One approach to achieving this with the PATH FORMER comprises the use of a thin stainless steel template with holes in it that would serve as a center-to-center locater. It could also act to contact the ECG electrode (or, if properly prepared, the template can serve directly as the ECG electrode) to provide the electrical path for depth determination through resistance trigger settings.

Thus, the operator would place the PATH FORMER nosepiece in each template opening and make a microconduit. This operation continues in a serial manner, in which several seconds are needed for the formation of each microconduit desired. For example, from about 1 to 5 minutes could be required to form 10 to 100 microconduits. In the alternative, the operator could freehand it, with the resulting microconduit location field being less ordered.

Yet another modification of the PATH FORMER comprises the addition of a sun gear with planet gears around it, each driving a cutter. This is preferably limited to 7 or 9 cutters, each forming microconduits on 0.125 inch centers, because of gear and shaft size constraints. In this embodiment, the closest hole centers would be about 0.125 inch. In addition, the depth sensing feature of the PATH FORMER would not be available on each cutter, but would instead be provided on a representative pilot cutter.

Another modification of the PATH FORMER apparatus is the currently preferred improvement, and it is based upon the recognition that human skin (epidermis & dermis) acts very much like a waterbed or a balloon on the microscopic level. If you press against the skin—particularly on those areas that have fatty tissue beneath them—it bulges out somewhere else. If you press against it with a circular ring, the ring sinks in somewhat causing the skin within and without the confines of the ring to bulge outwardly.

In view of this phenomenon, the preferred embodiment of this invention comprises a thin (0.0005 inch to 0.005 inch) sheet of stainless steel with holes (0.020 inch to 0.050 inch in diameter) that are about the same dimension close to each other, that can be attached like a drum head to a holding foot on the PATH FORMER apparatus. In this case, the motor in the PATH FORMER apparatus turns a flat disk bearing appropriate grit sandpaper or abrasive sponge. In operation, one presses the PATH FORMER foot against the skin in a body location underlaid with soft tissue. When adequate force is applied, the skin will bulge through the holes in the drum head. As the foot sinks in, the skin bulges up through the holes, and the sand paper disk or abrasive sponge moves down and sands off the top layer of the skin (the stratum corneum)—forming a multitude of microconduits at each hole of the drum head simultaneously.

The key to this embodiment of the invention is that the skin bulging through the holes in the stainless (or other material) drum head only protrudes very slightly above the inner (upper) side of the template, which limits the depth of the sanding process, keeping it above the level of the nerve net. Abrasives are commonly used by dermatologists to remove selected areas of the 0.0005 inch to 0.001 inch thick stratum corneum both for therapeutic purposes and cosmetic effects (dermabrasion and microdermabrasion). Suitable abrasives for removing skin tissue are well known and include various abrasive levels, e.g., fine, medium, course, etc. The stratum corneum could be pre-treated with alcohol or other drying chemical to make it less elastic and more abradable to speed up the process.

If one assumes that the bulge is approximately spherical, that implies that a circle of skin from about 0.0003 inch to 0.0005 inch in diameter extends above the upper surface of the template. Within a hole range of 0.040 inch to 0.070 inch, the protrusion would increase. These dimensions and centers would permit the formation of a 3×3 array of microconduits in a 0.250 inch square, or a 4×4 array in a 0.350 inch square. Experiments have shown that the bulging effect with 0.038 inch diameter holes on 0.046 inch centers in a 0.001 inch thick stainless steel template, allowed the skin to protrude up above the template surface by from 0.0002 inch to 0.0004 inch.

As used herein, the term "microconduit" refers to a small opening, channel, or hole into, or through, a tissue, that allows transfer of materials by liquid flow, and by electrophoresis. In one embodiment, a microconduit may also allow materials to move through by diffusion or by convection.

The average size of a microconduit according to an embodiment is about one (1) mm or less in diameter. In one embodiment, a microconduit has a diameter in the range of between about 10 micrometers and about 200 micrometers. In another embodiment, a microconduit has a diameter in the range of about between 2 micrometers and about one (1) mm. In an embodiment of the invention, a microconduit is usually smaller than needles used for syringe injections, but has a characteristic size or diameter that is much larger than the diameters of carriers of analyte molecules, therapeutic molecules and ions, or the diameters of analyte molecules, therapeutic molecules and ions themselves. As used herein, the term "diameter" refers to the approximate diameter or characteristic linear dimension of at least one cross-section of an approximately cylindrical-shaped section of a microconduit.

As described above, the present invention is directed to an improved version of the PATH FORMER device, which is fully described in US Patent Publication No. 2006-0041241 A1. A report on the use of the PATH FORMER device was published in Dermatologic Surgery, Vol. 32, No. 6, pages 828-833 (2006).

Figure 1:
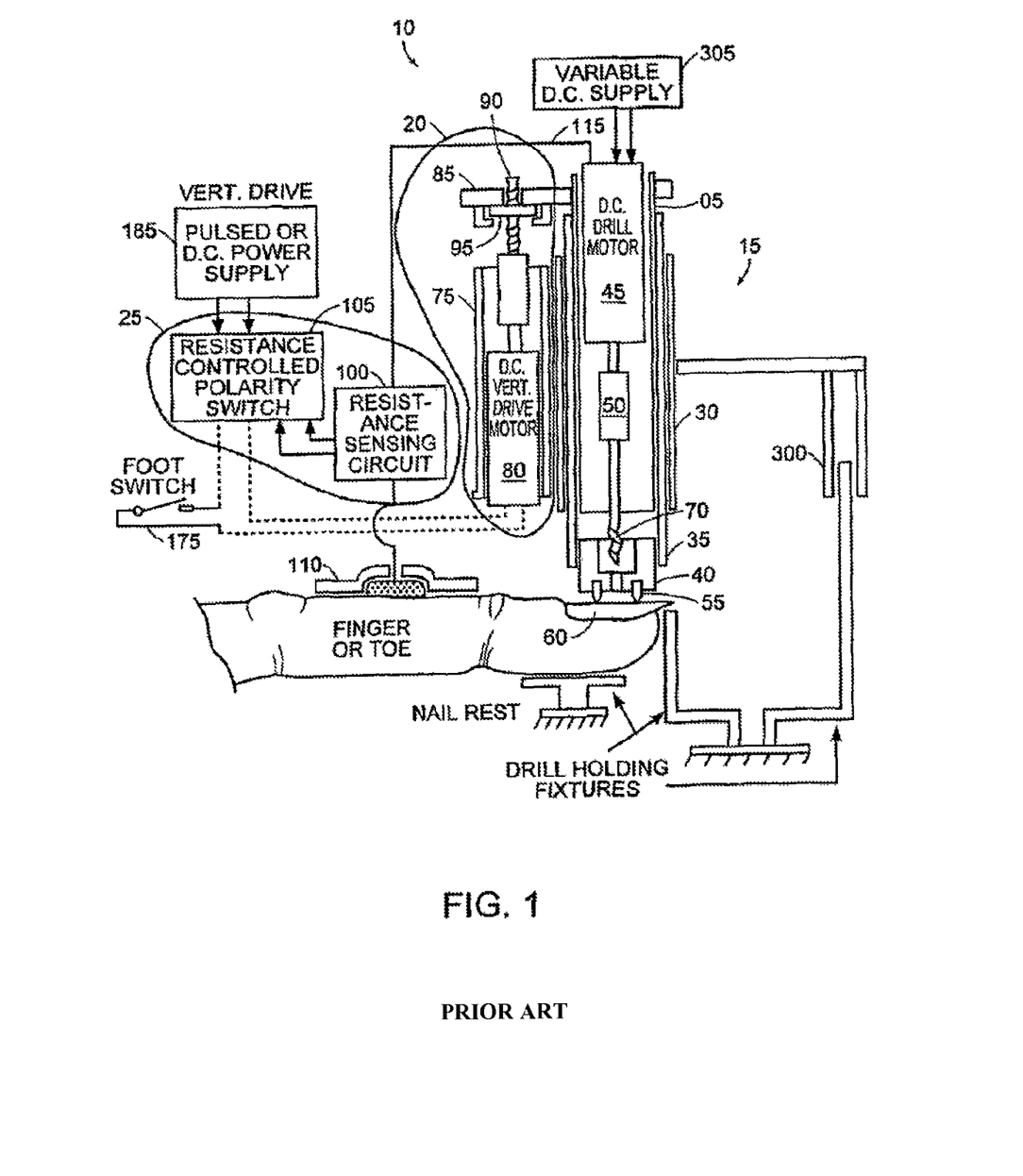
FIG. 1 shows the PATH FORMER device as copied from US Patent Publication No. 2006-0041241 A1. This prior art device is modified in the present invention as detailed herein.

FIG. 1 describes the PATH FORMER device. As shown therein, an impedance sensing drill 10 comprises a drilling assembly 15, a control module 20, mechanically connected to the drilling assembly 15 for controlling the depth of drilling by the impedance sensing drill 10; and a sensor 25, electrically connected to the drilling assembly 15 and control module 20 for detecting a change in an impedance of a material being drilled.

In a preferred embodiment the drilling assembly 15 comprises a first housing 30, a second housing 35 configured for mounting in the first housing 30, a third housing 05 slideably configured within the second housing 35, an electrically insulated nosepiece 40 attached to the second housing 35, a drill motor 45 electrically isolated from the third housing 05 and mounted within the third housing 05, and a drill collar 50 for receiving bits 70 used in drilling.

The first 30 and second 35 and third 05 housings are preferably made of metal and sized so that the third housing is slidable within the second housing while containing the drill motor 45. The drill motor 45 is preferably a dc motor with suitable power to form microconduits in the material being drilled, suitable d.c. motors include, but are not limited to, a micromotor by RMB Miniature Bearing of Ringwood N.J., and MOT 1009 or MOT 1025 by B.G. Micro of Garland Tex.

The nosepiece 40 is typically made of a non-conducting material so as to minimize the risk of electrical shock to tissue or organic matter the drill assembly is being used on. Also the nonconductive nosepiece eliminates any possible electrical impedance parallel paths between the drill/endmill "sensing electrode" and the resistance sensing circuit 100. The nosepiece 40 shown in FIG. 1, is made of plastic and typically contains three or four feet 55. These act to rigidly locate the entire drill assembly 15 to the outer surface of the material being drilled (here a nail 60). In other embodiments the nosepiece 40 may be adapted for use on other materials or surfaces. An example of such can be seen in FIG. 2 wherein the nosepiece 40a is made of Teflon and adapted for use on skin 65.

The nosepiece 40 shown in FIG. 1 is attached to the second housing 35. The second housing 35 is clamped by the first housing 30 in an adjustable manner. When unclamped, the nosepiece 40 can be positioned vertically with reference to the drill bit 70 and clamped. The first housing 30 is attached to the holding arm 300 that holds the entire mechanical assembly over the target area.

Referring again to FIG. 1, the collar 50, also referred to as a chuck, is preferably of a size and material suitable for attaching a bit 70 the drill motor 45. In a preferred embodiment the collar 50 is made out of an electrically conductive material allowing for electrical impedance sensing through the drill motor 45 to the drill bit 70 in contact with the material being drilled. Examples of suitable collar materials include, but are not limited to, stainless steel, brass and steel.

In preferred embodiments the control module 20 comprises a housing 75, a vertical drive motor 80, and a support arm 85. The housing 75 is preferably made of metal and attached to the first housing 30 of the drilling assembly 15. The vertical drive motor 80 is mounted in the housing 75. In preferred embodiments the vertical drive motor 80 is a d.c. motor. Suitable vertical drive motors include, but are not limited to micromotor by RMB Miniature Bearing of Ringwood N.J., and MOT 1009 or MOT 1025 by B.G. Micro of Garland Tex.

The support arm 85 is connected to the third housing 05 of the drilling assembly and mounted on a screw track 90 attached the vertical drive motor 80. In this configuration, as the vertical drive motor 80 rotates the support arm 85 travels along the screw 90 thereby raising or lowering the third housing 05 of the drilling assembly as well as the drill motor 45 and attached drill bit 70. The embodiment shown in FIG. 1 uses a captive nut 95 on the support arm 85 to effect the vertical movement along the screw track 90.

In a preferred embodiment the sensor 25 is electrically connected to the drill motor 45 of the drilling assembly 15 as well as the control module 20 for detecting a change in an impedance value of a material being drilled. In preferred embodiment the sensor 25 comprises a resistance sensing circuit 100, and a polarity switch 105. As shown in FIG. 1, the resistance sensing circuit 100 has a first electrode 110 placed in contact with the material of which electrical impedance is being measured. A second connection 115 is made from the resistance sensing circuit 100 to the drill motor 45 such that the drill bit 70, in electrical connection with the motor 45 though the collar 50, acts like a second electrode in contact with the material in which an electrical impedance change is being measured. The polarity switch 105 of the sensor 25 is electrically connected to the vertical drive motor 80 of the control module 20. When a change is detected in the impedance being measured a signal is sent to the control module 20 reversing the direction of the vertical drive motor 80.

In a preferred embodiment of the sensor 25, the electrical impedance characteristic being measured is electrical resistance. This measurement and drill control circuitry (25 and 185) are fully explained in US Patent Publication No. 2006-0041241 A1.

Referring again to FIG. 1, in a preferred embodiment the impedance sensing drill is typically mounted on a stand 300 in the proximity of the material being drilled. The drilling assembly 15, control module 20, and sensor 25 are connected to first 305 and second 185 power supplies. The first power supply 305 is a variable d.c. power supply for supplying electrical power to the drill motor. The second power supply 185 is either a variable or pulsed d.c. power supply for powering the vertical drive motor. Suitable power supplies include, but are not limited to a LP521FM by Lambada Co., Melville, N.Y., and a 721A, by Hewlett Packard Co., San Diego, Calif. The first electrode 110 is placed in contact with the material in which a microconduit is to be formed. The drilling of the microconduit is controlled by a switch 175, such as a foot pedal. An example of a suitable switch for controlling the drilling is a T-51-S, by Linemaster Switch Co., Woodstock, Conn. The user initiates drilling, by activating the control switch 175 (here a foot petal). When a change in the measured electrical impedance between first electrode 110 and the second electrode 70 (drill bit) is detected by the sensor 25, the sensor 25 sends a signal reversing the vertical direction of the drill, effectively stopping the drilling by removing the drill bit from the material.

Figure 2:
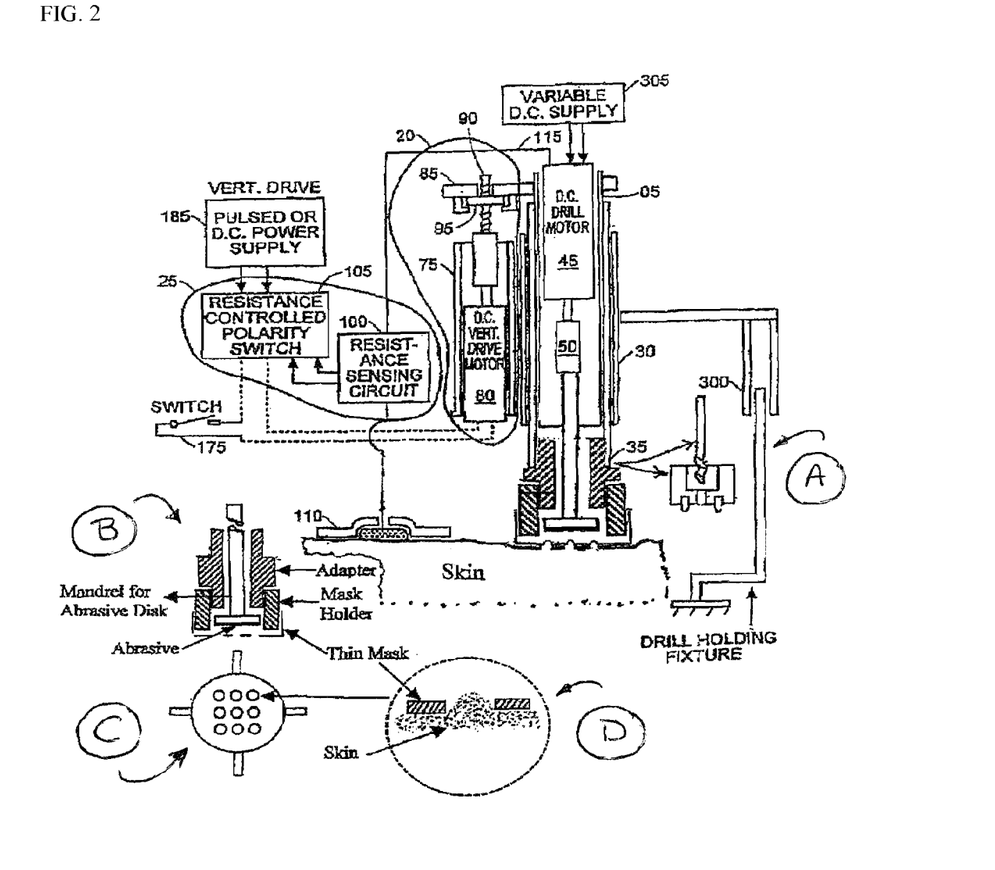
Figure 3:
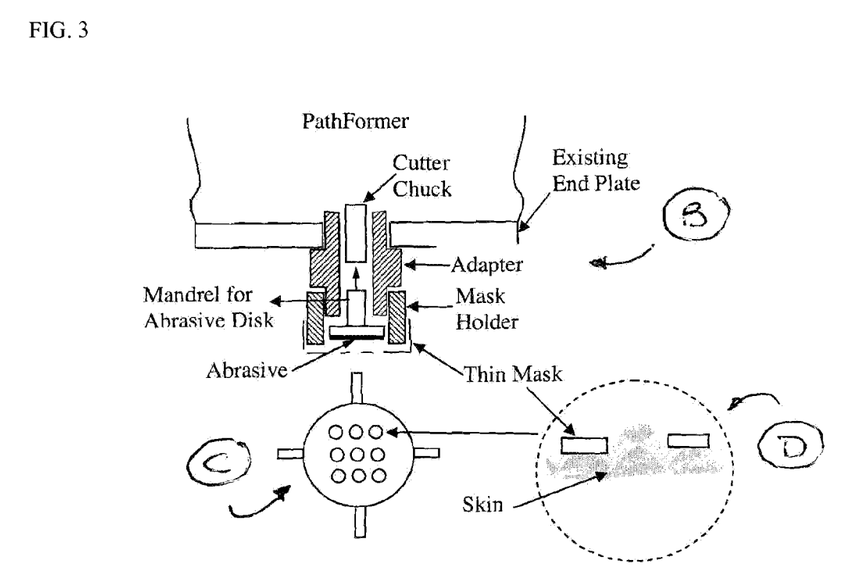
FIG. 3 is a close-up view of the modification made to the working end of the PATH FORMER device.

FIGS. 2 and 3 show the preferred modifications to be made to the device shown in FIG. 1. As shown at FIG. 2, Reference Point A, the drill bit 70 and nosepiece 40 are removed from the cutter chuck. They are replaced by a mandrel for an abrasive disk and a mask holder for a thin multi-hole mask.

Figure 4:
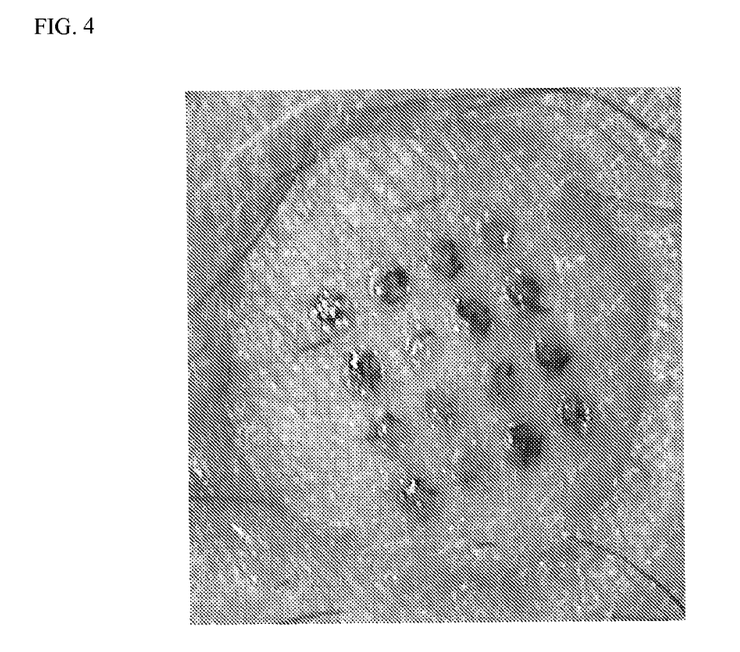
FIG. 4 illustrates multiple microconduits formed by the modified version of the PATH FORMER device.
Figure 5:
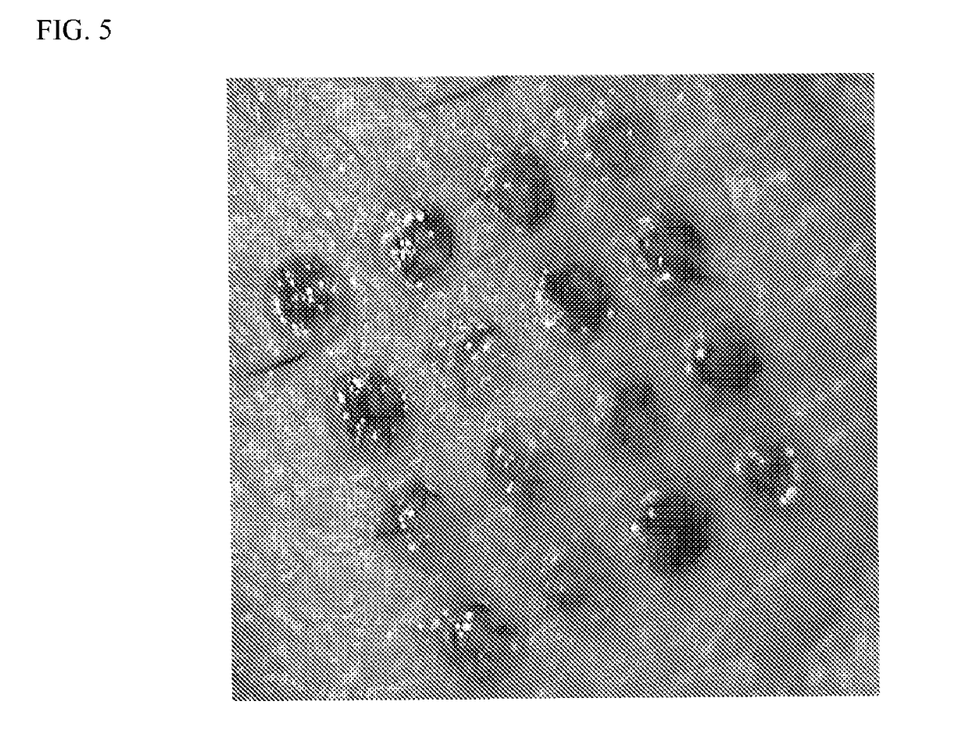
FIG. 5 is a close-up view of the multiple microconduits formed by the modified version of the PATH FORMER device.

As shown in FIGS. 2 and 3, at Reference Points C and D, the thin, multi-hole mask, when pressed into the surface of skin tissue, causes the skin to bulge through each of the holes in the mask, whereby the abrasive material on the abrasive disk, can remove it, leaving a number of microconduits. The size and depth of the microconduits is dictated by the size and number of holes in the multi-hole disk. Preferably at least three holes are present in the mask, more preferably at least 9 holes, and most preferably at least 16 holes. As illustrated in FIGS. 4 and 5, a mask with 16 holes has been successfully employed.

The components used to modify the PATH FORMER can be made from any suitable material, e.g., metal or plastic. Preferred metals are aluminum and stainless steel. An especially preferred metal for the multi-hole mask is stainless steel. Likewise, the abrasives used on the abrasive disk can be either permanent (e.g., diamond particles) or replaceable (e.g., abrasive pads). One abrasive material used in the testing phase was the material from a commercial Scotch-Brite pad.

Transdermal Delivery

Once a plurality of microconduits have been formed, such microconduits provide large aqueous pathways for molecular and ionic transport through the stratum corneum, the skin's main barrier to ionic and molecular transport. Because microconduit size, according to preferred embodiments, is much larger than even macromolecules such as proteins and nucleic acids, transport occurs with insignificant steric hindrance. For this reason, trans-stratum corneum microconduits or trans-corneal microconduits can provide transdermal transport of essentially any size molecule.

Thus, in yet another embodiment, the process of forming multiple microconduits can be followed by the additional step of transporting one or more therapeutic molecules or ions through one or more microconduits to achieve drug delivery to tissue, including skin, for example.

In one such embodiment, transdermal delivery of therapeutic agents (e.g., drugs such as insulin and genetic material such as DNA) is accomplished by forming a microconduit according to an embodiment of the invention, and then directing the therapeutic agent into the microconduit, thereby delivering the therapeutic agent through the skin to the tissue. In another embodiment, transdermal extraction of analytes is accomplished by forming a microconduit according to the invention and then removing the analyte from the tissue and through the microconduit, thereby removing the analyte from the tissue and through the microconduit. In one embodiment, the analyte is removed by sampling. For example, the analyte blood is removed by allowing the blood to flow out of a microconduit onto a collection sheet or plate. In another embodiment, an analyte such as interstitial fluid is removed by using, for example, a pipet to reduce pressure over the microconduit.

Many other examples of drugs and genetic material are well known, including drugs such as lidocaine and other anesthetics, heparin, erythropoietin, growth hormone, steroids, various peptides, and genetic material such as large DNA segments, RNA, small antisense oligonucleotides, and immunological material generally, including vaccines and adjuvants.

Transdermal delivery of therapeutic agents through a microconduit according to an embodiment is important for a number of reasons, including the fact that often the intact stratum corneum prevents therapeutically significant rates of molecular and ionic transport. Microconduits according to an embodiment allow sterically unhindered movement of molecules and ions through the stratum corneum. The movement of molecules and ions through a microconduit according to an embodiment may take place through diffusion, electrophoresis, or convection flow driven by hydrostatic pressure differences, and time varying pressure differences including ultrasound produced and osmotic pressure differences. This includes iontophoresis which can involve both electrophoresis and electro-osmosis. In one embodiment, a direct current voltage is applied to a microconduit to produce iontophoresis. In a particular embodiment, the direct current voltage applied to the microconduit is pulsed.

According to yet another embodiment, molecular and ionic movement through one or more microconduits with varying degrees of control can be achieved by using different amounts or concentrations of the molecules and ions supplied. According to an embodiment, molecular and ionic diffusion can be controlled by controlling the supply concentration of the molecules and ions, controlling the solution (usually based on physiologic saline) used, and establishing or measuring the temperature, and then controlling the time that the supply solution is in contact with one or more microconduits. One embodiment of the invention utilizes diffusion of a therapeutic agent in a suitable pharmaceutical carrier, such as a biocompatible, non-toxic liquid, through microconduits to achieve transdermal drug delivery. In another embodiment, in order to achieve sustained release of the therapeutic agent, a therapeutic agent is supplied in a hydrogel, polymer, or molecular matrix, rather than in a liquid solution.

The invention also relates to a delivery method and apparatus, such that immunizing material can be effectively introduced into the tissue near dendritic cells, and other cells such as keratinocytes, and then, as a further step, delivery into the dendritic cells, keratinocytes, and any other target cells within the skin.

According to an embodiment, the process of forming one or more microconduits is followed by the additional step of transporting immunizing material into the tissue. Cutaneous immunization in which immunizing material is delivered to dendritic cells within the skin is of particular interest. Thus, formation of transdermal microconduits that fully penetrate the stratum corneum can be followed by transport of immunizing material into the epidermis.

This process includes the transport or delivery of nucleic acids such as DNA into the skin for the purpose of cutaneous immunization. According to an embodiment, a solution containing nucleic acids is applied to the skin surface into which microconduits have been formed, and diffusion, electrophoresis or convection are used to transport nucleic acid molecules through one or more microconduits into the skin tissue.

One or more nucleic acid molecules can also be transported through microconduits into skin tissue for the purpose of gene therapy.

In an embodiment of the invention, because of the size of the microconduits, liquid convection flow operates naturally to move molecules through each microconduit. Convection flow is important if no molecular matrix has been formed within the microconduit. In one embodiment, water soluble molecules are delivered by providing a driving force for convection through one or more microconduits. According to an embodiment, a pressure difference or pressure gradient is utilized to drive flow. For example, a pressure difference can be formed by applying an increased pressure with respect to the pressure within the tissue, at the terminus (entrance or opening) of a microconduit. If the surface opening of a microconduit is adjacent to a reservoir with a drug-containing solution of the molecule to be delivered, then increasing the pressure within the reservoir creates a pressure difference along the microconduit, and flow results. This is analogous to applying pressure to the solution within the barrel (reservoir) of a syringe: Increasing the barrel pressure drives flow through the needle (analogous to a microconduit) into a tissue. Thus, if transdermal drug delivery by convection through one or more microconduits is desired, flow can be established, according to an embodiment, by elevating the pressure in a drug reservoir that is held against the skin at the sites of one or more trans-stratum corneum microconduits. For example, in a particular embodiment, the drug or therapeutic agent directed into the opening is in a column, for example, a pipet or capillary tube, and the column is sealed to the tissue around the microconduit. Next, pressure is directly applied to the microconduit, for example, by squeezing a rubber bulb attached to one end of the column or pipet, thereby forcing the therapeutic agent included in the column or pipet into the microconduit. The therapeutic agent is absorbed by the tissue surrounding the microconduit. According to another embodiment, convection through microconduits can also be established by using an osmotic pressure difference, a time varying pressure difference such as ultrasound, and electro-osmosis.

According to yet another embodiment, pressure can also be used to force a deformable drug-containing hydrogel from a reservoir or supply into the microconduits. When inserted into a microconduit according to an embodiment, the hydrogel can provide slow, controlled release of drug into the epidermis, or into deeper tissues if the microconduit penetrates beyond the epidermis. Generally, molecules released into the epidermis migrate so as to enter blood capillaries. Other types of slow release entities of small size can also be introduced through microconduits.

EXAMPLES

In considering how to make multiple microconduits through the stratum corneum simultaneously, the idea of sanding off at least a portion of the stratum corneum was considered. Unlike the Microscission System (see, U.S. Pat. No. 6,706,032, incorporated herein by reference) in which tiny, sharp microscopic aluminum oxide particles in a gas stream are used to cut bits of tissue that are carried away by the gas flow, this concept arises from the use of an abrasive, for example, sandpaper with hard, sharp particles adhered to it. Since the stratum corneum is fairly dry, somewhat hard and thin, sliding sandpaper over it will abrade it—as opposed to other tissues that are hydrated, softer to very soft and thus move around under abrasive particles moving on them. In fact, using sandpaper or similar abrasives to remove the stratum corneum is one standard technique in dermatology and transdermal absorption work.

Knowing the waterbed or pillow-like nature of the epidermis and dermis from past work with Microscission and Mesoscission Systems, the idea of a thin, rigid plate having sufficiently large holes through it to permit the stratum corneum, epidermis and dermis tissues to bulge through the holes when pressed against it firmly was developed. The idea would be to determine the hole diameter to produce a protrusion of skin extending beyond the side of the rigid plate opposite the skin. If sandpaper were passed over this 'Gaussian Curve'—like protrusion while it was pressed through the hole(s), and if the stratum corneum were dry enough, the abrasive material on the sandpaper would remove the relative hard stratum corneum to produce an opening through the stratum corneum that would be approximately circular. The depth of this opening would have to be a bit greater than the stratum corneum's nominal thickness (0.0005 to 0.001 inch) to assure an open path into the epidermis. The analogue to this would be an electric razor with holes in the cutting head through which hairs of the beard can protrude to be cut off by sharp blades passing over them.

Modification of the PATH FORMER into a Multi Microconduit Cutter (MMC)

After preliminary experiments with thin (0.001 to 0.002 inch thick) stainless steel shim stock having a variety of holes drilled through and pressed against the subject's forearm and back of hand, it was determined that holes at least 0.040 inch diameter were needed to permit the skin against which the metal was pressed to protrude through and above the metal.

Also, the question of how rigid would this screen have to be was tested. Here the diameter of the screen contact was found to be perhaps 0.375 to 0.50 inch. This is because the larger the screen contact is, the more it is deflected and the less it sinks into the skin, and at some point, the contacted skin is no longer stretched and thus no longer protrudes through the screen openings adequately. Finally, if the screen is stiff enough, the material remaining between holes can be minimized both for better packing density and to permit the maximum height of the skin protrusions.

After these parameters were addressed, an attachment was made for the PATH FORMER. The screen was to be 0.002 inch thick stainless steel (0.001 inch) had deflected too much when pressed against skin. It would have 9 openings, 0.050 inch diameter on 0.070 inch centers, giving a between-hole metal width of 0.020 inch. The diagonal of this square array is 0.250 inch. Since this must be easily removed for abrasive (e.g., sandpaper) replacement, a holding 'nose' was made 0.550 inch long with a 0.260 inch long, 0.345 inch outside diameter, 0.255 inch inside diameter to which the screen was attached by means of double sided sticky tape or attached by a suitable glue. This was integral with a 0.306 inch long by 0.50 inch outer diameter collar.

The foot was replaced with a tubular adapter section that fit into the PATH FORMER hole for the foot, with its other end fitting into the collar of the screen section—which had a locking screw to hold the screen collar to the adapter section.

The abrasive (sandpaper) holder consisted of a shaft to fit in the 0.125 inch diameter cutter chuck that had a 0.230 inch diameter, flat ended section on the other end. An abrasive (sandpaper) disk was attached to this with double sided sticky tape. In another embodiment an abrasive sponge was attached with sticky tape. In a third embodiment, a thinner sponge-like material was sticky-taped to the mandrel and the sandpaper disk was sticky taped to the sponge-like material. This arrangement allowed the somewhat stiff sandpaper to tilt and conform to misalignment and lack of parallelism between the screen and sandpaper.

The PATH FORMER was further modified by drilling and tapping the end plate holding the foot/adapter for a stop screw to permit adjusting maximum forward motion of the carriage and thus the sanding disk to allow the disk to approach the skin-pressed screen and stop perhaps 0.0005 inch to 0.001 inch before touching it to allow the disk to touch the thru-hole protruding skin domes without hitting the back of the screen.

After some adjustments to obtain the best sandpaper to screen spacing, the inventor was able to open several microconduits simultaneously. There was only the very slightest sensation during the process of forming the microconduits. There was no active bleeding from the microconduits. See FIGS. 4 and 5.

What is claimed is:

1. Apparatus for the simultaneous formation of multiple microconduits in a flexible material by abrasion, said apparatus comprising an abrasion assembly including a rotating abrading device and a control module electromechanically connected to the abrasion assembly for controlling the abrasion by stopping and pulling back the abrading device, wherein the abrasion assembly further includes a mask with a plurality of holes therein and an abrasive disk for the formation of multiple microconduits via abrasion of the flexible material protruding through each of the holes in the mask, wherein the abrasion assembly also includes an impedance sensing unit and a sensor electrically connected to the mask.

2. The apparatus of claim 1, wherein the abrasive disk includes a permanent abrasive material.

3. The apparatus of claim 1, wherein the abrasive disk includes a replaceable abrasive material.

4. The apparatus of claim 1, wherein the abrasive disk includes a permanent abrasive material.

5. The apparatus of claim 1, wherein the abrasive disk includes a replaceable abrasive material.

6. The apparatus of claim 1, further comprising a mount that allows the abrasion assembly to move in a direction perpendicular to the surface being abraded.

7. The apparatus of claim 1, further comprising a mount that allows the abrasion unit to move in a direction perpendicular to the surface being abraded.

8. The apparatus of claim 1, wherein the control module is computer controlled.

9. The apparatus of claim 1, wherein the thickness of the mask sets the depth of the microconduits.

10. The apparatus of claim 1, wherein the diameter of the openings in the mask sets the depth of the microconduits.

11. The apparatus of claim 1, wherein the mask comprises a stainless steel screen about 0.002 inches thick with a diameter of from 0.375 to 0.50 inch, the screen having a plurality of holes, each hole being at least 0.040 inch in diameter.

12. The apparatus of claim 11, wherein the mask comprises three holes, each hole being 0.050 inch in diameter, on 0.070 inch centers, giving a between-hole width of 0.020 inch.

13. The apparatus of claim 11, wherein the mask comprises nine holes, each hole being 0.050 inch in diameter, on 0.070 inch centers, giving a between-hole width of 0.020 inch.

14. The apparatus of claim 11, wherein the mask comprises sixteen holes, each hole being 0.050 inch in diameter, on 0.070 inch centers, giving a between-hole width of 0.020 inch.

15. The apparatus of claim 1, further comprising a mask holder comprising a cylindrical member 0.550 inch long, 0.345 inch outside diameter, and 0.255 inch inside diameter, to which the screen is attached.

16. The apparatus of claim 15, further comprising a tubular adapter comprising a cylindrical member for mounting the mask holder to the end of the apparatus.

17. The apparatus of claim 1, further comprising an abrasive holder comprising a shaft with a 0.230 inch diameter flat ended section on the end.

* * * * *